United States Patent
Carim et al.

(10) Patent No.: US 8,333,718 B2
(45) Date of Patent: *Dec. 18, 2012

(54) WEIGHTED BIOACOUSTIC SENSOR AND METHOD OF USING SAME

(75) Inventors: Hatim M. Carim, West St. Paul, MN (US); Vivek Bharti, Cottage Grove, MN (US); Fred L. DeRoos, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/211,178

(22) Filed: Aug. 16, 2011

(65) Prior Publication Data

US 2011/0301503 A1 Dec. 8, 2011

Related U.S. Application Data

(63) Continuation of application No. 11/287,179, filed on Nov. 23, 2005, now Pat. No. 7,998,091.

(51) Int. Cl.
- *A61B 7/00* (2006.01)
- *A61B 5/08* (2006.01)
- *A61B 7/04* (2006.01)
- *G01N 1/00* (2006.01)
- *G10K 11/00* (2006.01)
- *H04R 25/00* (2006.01)

(52) U.S. Cl. ......... 600/586; 600/534; 600/535; 73/652; 181/131; 381/67

(58) Field of Classification Search .......... 73/431, 73/649; 181/126, 131, 132, 137, 167; 600/534, 600/535, 586; 381/67

See application file for complete search history.

(56) References Cited

U.S. PATENT DOCUMENTS

| | | | |
|---|---|---|---|
| 3,182,129 A | 5/1965 | Clark | |
| 3,682,161 A | 8/1972 | Alibert | |
| 4,008,408 A | 2/1977 | Kodama | |
| 4,012,604 A | 3/1977 | Speidel | |
| 4,127,749 A | 11/1978 | Atoji | |
| 4,295,471 A | 10/1981 | Kaspari | |
| 4,672,976 A | 6/1987 | Kroll | |
| 4,708,019 A | 11/1987 | Rubner | |

(Continued)

FOREIGN PATENT DOCUMENTS

CN 2162654 Y 4/1994

(Continued)

OTHER PUBLICATIONS

Bizet et al., 1999, *Analusis*, pp. 609-616, Wiley-VCH. "Biosensors Based on Piezoelectric Transducers.".

(Continued)

*Primary Examiner* — Max Hindenburg
*Assistant Examiner* — Adam Eiseman
(74) *Attorney, Agent, or Firm* — Kevin W Weber

(57) ABSTRACT

A sensor for sensing bioacoustic energy includes a housing comprising an interfacing portion configured to establish coupling with a body part during use. The sensor includes a transducer element coupled to the interfacing portion of the housing and configured to sense sounds produced by matter of biological origin. One or more conductors are coupled to the transducer element. A mass element is compliantly coupled to a surface of the transducer element. Intervening material is disposed between the transducer element surface and the mass element, and allows for differential motion between the transducer element surface and the mass element during excitation of the transducer element.

26 Claims, 6 Drawing Sheets

U.S. PATENT DOCUMENTS

| | | | |
|---|---|---|---|
| 4,855,544 | A | 8/1989 | Glenn |
| 4,884,809 | A | 12/1989 | Rowen |
| 5,036,857 | A | 8/1991 | Semmlow |
| 5,365,937 | A | 11/1994 | Reeves |
| 5,425,750 | A | 6/1995 | Moberg |
| 5,496,352 | A | 3/1996 | Renger |
| 5,497,426 | A | 3/1996 | Jay |
| 5,539,831 | A | 7/1996 | Harley |
| 5,566,671 | A | 10/1996 | Lyons |
| 5,610,987 | A | 3/1997 | Harley |
| 5,807,268 | A | 9/1998 | Reeves |
| 5,834,650 | A | 11/1998 | Kim |
| 5,853,005 | A | 12/1998 | Scanlon |
| 5,913,829 | A | 6/1999 | Reeves |
| 6,002,963 | A | 12/1999 | Mouchawar |
| 6,028,942 | A | 2/2000 | Greenberger |
| 6,261,237 | B1 | 7/2001 | Swanson |
| 6,324,289 | B2 | 11/2001 | Orten |
| 6,347,147 | B1 | 2/2002 | Downs, Jr. |
| 6,478,744 | B2 | 11/2002 | Mohler |
| 6,486,588 | B2 | 11/2002 | Doron |
| 6,661,161 | B1 | 12/2003 | Lanzo |
| 6,806,622 | B1 | 10/2004 | Schmidt |
| 6,852,084 | B1 | 2/2005 | Boesen |
| 6,988,993 | B2 | 1/2006 | Sullivan |
| 2003/0214200 | A1 | 11/2003 | Thompson |
| 2004/0032957 | A1 | 2/2004 | Mansy |
| 2005/0014999 | A1 | 1/2005 | Rahe-Meyer |
| 2005/0043643 | A1 | 2/2005 | Priemer |
| 2005/0200242 | A1 | 9/2005 | Degertekin |
| 2005/0201576 | A1 | 9/2005 | Barker |
| 2005/0232434 | A1 | 10/2005 | Andersen |
| 2007/0113649 | A1 | 5/2007 | Bharti |

FOREIGN PATENT DOCUMENTS

| | | |
|---|---|---|
| CN | 1159573 | 9/1997 |
| DE | 932268 | 8/1955 |
| DE | 2453926 | 5/1976 |
| DE | 2703781 | 8/1978 |
| EP | 0801927 | 10/1997 |
| EP | 0716628 | 2/1998 |
| EP | 0659058 | 1/1999 |
| GB | 2051584 | 7/1980 |
| JP | 62-091825 | 4/1987 |
| JP | 4317638 | 11/1992 |
| JP | 04335797 | 11/1992 |
| JP | 2004077346 | 3/2004 |
| WO | WO 95/34917 | 12/1995 |
| WO | WO 96/27407 | 9/1996 |
| WO | WO 99/53277 | 10/1999 |
| WO | WO 00/10462 | 3/2000 |
| WO | WO 01/78059 | 10/2001 |
| WO | WO 01/97675 | 12/2001 |
| WO | WO 03/011132 | 2/2003 |
| WO | WO 04/002191 | 12/2003 |
| WO | WO 2004/105612 | 12/2004 |

OTHER PUBLICATIONS

Measurement Specialties, Inc., (Apr. 2006), www.meas-spec.com, p. 22. "MiniSense 100 Vibration Sensor."
Supplementary European Search Report dated Apr. 2010, 2 pgs.

WEIGHTED BIOACOUSTIC SENSOR AND METHOD OF USING SAME

CROSS REFERENCE TO RELATED APPLICATIONS

This application is a continuation of U.S. application Ser. No. 11/287,179, filed Nov. 23, 2005, issued as U.S. Pat. No. 7,998,091, the disclosure of which is incorporated by reference in its entirety herein.

FIELD OF THE INVENTION

The present invention relates to medical sensing devices and, more particularly, to sensors and devices incorporating such sensors whose input is variations of bioacoustic energy and output is a conversion to another form of energy.

BACKGROUND

A variety of devices have been developed to detect sounds produced by the body, such as heart sounds. Known devices range from primarily mechanical devices, such as the stethoscope, to various electronic devices, such as microphones and transducers. The stethoscope, for example, is a fundamental tool used in the diagnosis of diseases and conditions of the cardiovascular system. It serves as the most commonly employed technique for diagnosis of such diseases and conditions in primary health care and in circumstances where sophisticated medical equipment is not available, such as remote areas.

Although many electronic stethoscopes are available on the market, they have yet to gain universal acceptance by the physicians and other medical practitioners. Possible reasons for non-acceptance of electronic stethoscopes include the production of noise or artifacts that disturb the clinician during patient evaluation, as well as limitations associated with amplification and reproduction of certain biological sounds of interest. For example, a biological sound may be present but masked by noise, or wholly absent, and many conventional electronic stethoscopes are not capable of distinguishing between these two cases.

Noise that impacts stethoscope performance may be defined as any signal other than that of interest. Various types of noise include external or ambient noise, noise related to auscultation, noise generated by the electronic circuits of the stethoscope, and noise of biological nature produced by the patient's body, for example.

There is a need for a bioacoustic sensor with improved sensitivity and robustness. There is a further need for such a sensor that may be incorporated in various types or medical sensing devices, such as stethoscopes, that provides for an improved signal-to-noise ratio relative to conventional implementations. The present invention fulfills these and other needs.

SUMMARY OF THE INVENTION

The present invention is directed to sensors for sensing bioacoustic energy and methods for using same. According to an embodiment of the present invention, a bioacoustic sensor includes a housing comprising an interfacing portion configured to establish coupling with a body part during use. The sensor includes a transducer element coupled to the interfacing portion of the housing and configured to sense sounds produced by matter of biological origin. One or more conductors are coupled to the transducer element. A mass element is compliantly coupled to a surface of the transducer element.

Intervening material is disposed between the transducer element surface and the mass element. The intervening material allows for differential motion between the transducer element surface and the mass element during excitation of the transducer element. The intervening material preferably comprises an adhesive, such as a pressure sensitive adhesive. The intervening material is capable of transmitting sound signals, and has a low acoustic impedance.

The mass element, intervening material, and transducer element surface are configured to allow for mechanical deformation of the transducer element in response to bioacoustic energy impinging on the transducer element. Preferably, the mass element, intervening material, and transducer element are configured to effectively amplify a signal producible by the transducer element. Increased signal production by the transducer element may involve reducing loss of bioacoustic energy transferred to the transducer during excitation.

The mass element may cover substantially all of an effective transducing portion of the transducer element surface. Alternatively, the mass element may cover less than all of an effective transducing portion of the transducer element.

The mass element may comprise a mass and a stiff sheet or membrane having a first surface and a second surface, and the mass itself has a stiff surface. The first surface of the stiff sheet or membrane may be arranged to contact the intervening material, and the mass may be disposed adjacent the second surface.

In one implementation, a polyvinyledene fluoride-like piezoelectric film (e.g., a PVDF2 film) is encased in a polyester film as if in a pouch. A polyester film of about 1.5 thousandths of an inch thick may be disposed on each side of the PVDF2 film, for example. In another implementation, the transducer element may comprise a laminate structure. The laminate structure may comprise a piezoelectric film, a weight in film form, and one or more adhesive layers.

The mass element may comprise metal, non-metallic material, or composite material. The mass element may have a substantially uniform weight distribution profile relative to an x-y plane of the transducer element. The mass element may alternatively have a substantially linear weight distribution profile relative to an x-y plane of the transducer element. In other configurations, the mass element may have a substantially non-linear weight distribution profile relative to an x-y plane of the transducer element. The mass element may comprise a unitary mass or a plurality of discrete mass arrangements.

The transducer element is preferably configured to modulate or generate an electrical signal in response to deformation of the transducer element. The transducer element may comprise piezoelectric material, such as a polymeric piezoelectric film, or a piezoresistive or piezo-ceramic material or element. The transducer element may comprise one or more strain gauges or one or more capacitive elements. The transducer element may be planar or non-planar, such as in the case of a curved or corrugated configuration.

The housing of the sensor may be configured for hand-held coupling to a body part during use. The sensor may include a fixing arrangement coupled to the housing and configured to establish affixation between the housing and the body part during use. For example, the sensor may include an adhesion arrangement coupled to the housing and configured to establish adhesive coupling between the housing and the body part during use.

One or more conductor are coupled to the transducer element, which may be electrical conductors. In another configuration, the conductor(s) coupled to the transducer element may include at least one optical conductor. The optical conductor may be coupled to converter circuitry. The converter circuitry may be situated remote from the sensor and configured to convert a received optical signal to an output electrical signal. The converter circuitry may be coupled to one or more electrical-to-audio converters, such as a pair of earphones. The converter circuitry may be coupled to an interface configured to couple the converter circuitry to an electronic device situated remote from the sensor.

The housing of the sensor may include a base and a cover. The base may include the interfacing portion and the cover may be coupled to the base via a compliant joint arrangement. The cover may include acoustically absorptive material. The interfacing portion of the housing may range in stiffness from relatively pliable to substantially stiff or rigid. The interfacing portion of the housing may include or be formed from a polymeric material, a metal or alloy, a composite material, or a ceramic or crystalline material.

A sensor unit may be implemented that includes two or more transducer elements of a type described herein, wherein each of the transducer elements is configured to have a different frequency response. For example, each of the transducer elements has a stiffness, weight, shape, and thickness, and at least one of the stiffness, weight, shape, and thickness of each transducer element differing from that of other transducer elements of the sensor. Each of the transducer elements may be supported from the housing by a common anchoring arrangement or by separate anchoring arrangements.

Gain control circuitry may be provided so that a gain response of each transducer element may be selectably adjustable. Noise cancellation circuitry may be provided, which may include an auxiliary transducer element disposed within the housing other than at the interfacing portion of the housing. Noise cancellation circuitry may be coupled to the transducer element and the auxiliary transducer.

A stethoscope may be implemented to include a sensor of a type described herein. The sensor of the may include a single transducer element or a multiplicity of transducer elements of a type described herein. A helmet may be implemented to include one or more sensors of a type described herein, and may include noise cancellation circuitry.

A sensor may be implemented to include communications circuitry configured to facilitate wired or wireless communication between the sensor and a device external of the housing. A sensor may include signal processing circuitry, such as a digital signal processor, coupled to the transducer element. The signal processing circuitry may be configured to filter and/or perform analyses on a sense signal produced by the transducer element.

In accordance with a further embodiment, a method of sensing bioacoustic energy involves exciting a transducer in response to the bioacoustic energy. The method further involves reducing loss of the bioacoustic energy transferred to the transducer during excitation. The method also involves modulating or generating a signal by the transducer in response to excitation of the transducer. Reducing loss of the bioacoustic energy may involve facilitating differential motion between the transducer and a stiff mass during excitation of the transducer.

Establishing coupling may involve establishing hand-held coupling between the interfacing portion of the sensor housing and the body part. Coupling between the interfacing portion and the body part may be established via adhesion or a restraining arrangement fixable to the body.

The signal modulated or generated by the transducer may be an electrical signal, and the method may further involve converting the electrical signal to an optical signal and transmitting the optical signal remotely of the sensor housing. A frequency response of the transducer element may be modified. Noise cancellation may be performed using the transducer element and at least one auxiliary transducer element. Communication may be established between a device disposed within the sensor housing and a device external of the sensor housing. Various forms of analog and/or digital signal processing and/or analyses may be performed on the signal modulated or generated by the transducer.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
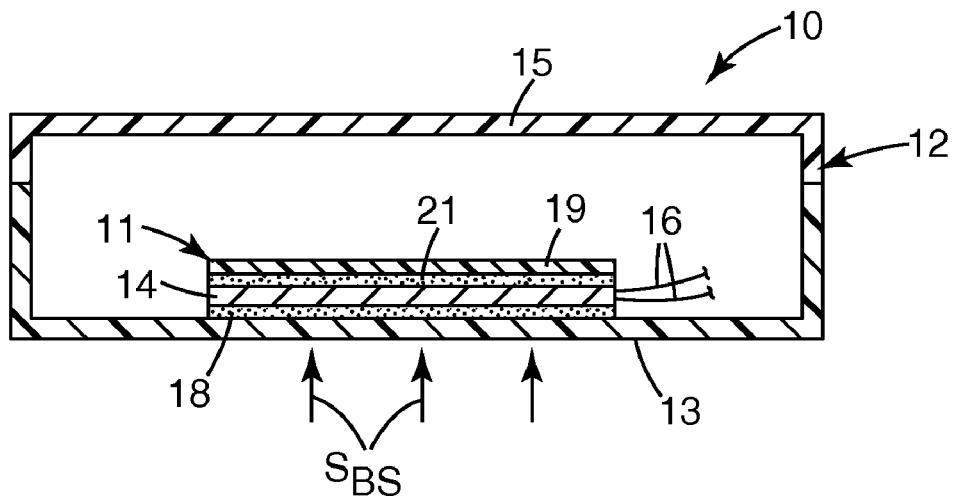
FIG. 1 is a diagram of a sensor that incorporates a transducer assembly that includes a weighted transducer element in accordance with an embodiment of the present invention.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF VARIOUS EMBODIMENTS

In the following description of the illustrated embodiments, reference is made to the accompanying drawings that form a part hereof, and in which is shown by way of illustration, various embodiments in which the invention may be practiced. It is to be understood that the embodiments may be utilized and structural changes may be made without departing from the scope of the present invention.

The present invention relates to sensors that are configured to be sensitive to sounds produced by matter of biological origin and methods for using same. Sensors and devices incorporating such sensors include those configured for auscultation, and may be configured to be sensitive to sounds produced by the heart, lungs, vocal cords, or other organs or tissues of the body, for example. By way of example, a sensor of the present invention may be incorporated in an electronic stethoscope, a helmet, or other externally worn or coupled apparatus or instrument that senses sounds produced by the body. A sensor of the present invention may also be configured for temporary or permanent fixation within the body, such as a heart or lung sound monitor implanted within the body, for example.

Sensors of the present invention may be implemented to be preferentially sensitive to a range of frequencies associated with human hearing. It is understood, however, that frequencies associated with body sounds below and/or above the auditory range of frequencies may also be sensed by sensors of the present invention. For example, sensors of the present invention may be implemented to sense body sounds that have frequencies ranging between just above DC and about 25 kHz. Sensors of the present invention may produce an audible output that falls within the auditory frequency range, or may produce an electrical or optical sensor that includes content above and/or below the auditory frequency range.

Bioacoustic sensors of the present invention preferably incorporate a transducer that is configured to modulate or generate an electrical signal in response to deformation of the transducer. Suitable transducers are those that incorporate piezoelectric material (organic and/or inorganic piezoelectric material), piezoresistive material, strain gauges, capacitive or inductive elements, a linear variable differential transformer, and other materials or elements that modulate or generate an electrical signal in response to deformation. Suitable piezo materials include polymer films, polymer foams, ceramics, composite materials or combinations thereof. Additionally, the present invention may incorporate arrays of transducers of the same or different transducer type and/or different transducer materials, all of which may be connected in series, individually, or in a multi-layered structure.

The inventors have found that a bioacoustic sensor incorporating a weighted or stiffened piezoelectric film transducer implemented according to the present invention, for example, provides for a significantly improved sensitivity over conventional piezoelectric film transducer arrangements. The sensitivity of a weighted piezoelectric film transducer may be enhanced by the addition of a stiff sheet, film, or membrane disposed between the transducer element and mass. For example, use of a stiff sheet of sufficient mass may provide for significantly improved transducer sensitivity. In one experiment, sensor sensitivity was improved by more than 25 times by addition of a mass compliantly coupled to the piezoelectric film transducer element. A suitable piezoelectric film for a bioacoustic sensor of the present invention include those disclosed in U.S. Pat. Nos. 4,434,114; 4,365,283; and 5,889,873, which are hereby incorporated herein by reference.

Turning now to the figures, FIG. 1 illustrates a sensor 10 that incorporates a transducer assembly 11 which includes a weighted transducer element in accordance with an embodiment of the present invention. According to the embodiment of FIG. 1, a sensor 10 includes a housing 12 to which a transducer assembly 11 is mounted. The transducer assembly 11 includes a transducer 14 which is supported by, or otherwise connected to, the housing 12 via anchoring arrangement 18. The transducer 14 includes one or more electrical contacts that allow for connection(s) to one or more conductors 16. The conductors 16 are typically electrical conductors or wires, but may alternatively be optical fibers coupled to electrical-to-optical converter circuitry, as in the case of an embodiment discussed hereinbelow.

In the embodiment shown in FIG. 1, the transducer 14 is mounted to the housing 12 so that vibrations resulting from body sounds, $S_{BS}$, impinging on an interfacing portion 13 of the housing 12 are readily communicated to the transducer 14. Many mounting configurations are contemplated that permit the transducer 14 to receive vibrations transmitted to the transducer 14 via the interfacing portion 13 of the housing 12.

The transducer 14 shown in FIG. 1 is affixed to the housing 12 by way of anchoring arrangement 18. The anchoring arrangement 18 may rigidly or compliantly couple the transducer 14 to the interfacing portion 13 of the housing. For example, the anchoring arrangement 18 may be an epoxy, a chemical bond, a weld or solder joint, a screw(s)/nut(s), rivet (s) or other mechanical coupling, or pressure sensitive adhesive, for example. A suitable anchoring arrangement 18 may include No. 924 Scotch Adhesive Transfer Tape or No. DP100 Scotch Weld epoxy adhesive, both available from 3M, St, Paul, Minn. It is believed that less compliant fixation arrangements should provide for better transmission of vibrations from the interfacing portion 13 of the housing to the transducer 14.

Further shown in FIG. 1 is a mass 19 which is compliantly coupled to the transducer 14 by way of intervening material 21. The intervening material 21 disposed between the transducer 14 and mass 19 is a material capable of transmitting sound signals. The intervening material 21 also allows for differential motion between the transducer 14 and the mass 19 during excitation of the transducer 14. Allowance of differential motion between the mass 19 and transducer 14 allows for mechanical deformation of the transducer element 14, which is a necessary condition for the transducing element of the transducer 14 to function properly.

The intervening material 21 may be an adhesive layer, such as a pressure sensitive adhesive layer. Other types of intervening material 21 include No. 732 Silicone Sealant, available from Dow Corning, Midland. Mich., or one or more layers of No. 924 Scotch Adhesive Transfer Tape, available from 3M, St. Paul, Minn. The intervening material 21 may include a foam material, such as an open cell polyurethane low-density foam. The intervening material 21 preferably has a low acoustic impedance.

Additionally, the mass 19 provides a relatively stiff backing to the transducer 14. The stiff backing offered by the mass 19 enhances the transducer's ability to generate an electric signal by vibrating or flexing, or in a compression mode, as a result of the acoustic wave energy impinging on the housing 12. The mass 19, intervening material 21, and transducer operate together to effectively amplify a signal producible by the transducer 14.

The mass 19 may covers substantially all of an effective transducing portion of the transducer 14, as is shown in FIG. 1. Alternatively, the mass 19 may cover less than all of an effective transducing portion of the transducer 14. The mass 19 may be formed of metal, a non-metallic material such as a polymeric material, or a composite material, for example. It is desirable that at least the surface of the mass 19 facing the transducer 14 possess a high reflection coefficient to acoustic waves of interest and their Fourier frequency range. Generally, materials that are hard and dense, such as metals and their alloys and ceramics, are suitable.

Figure 2:
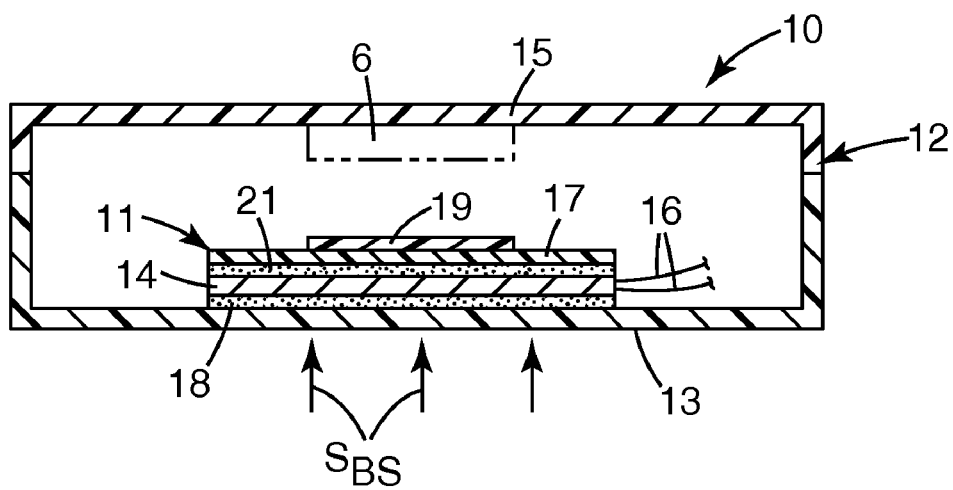
FIG. 2 is a diagram of a sensor that incorporates a transducer assembly that includes a stiffening sheet or membrane and a weighted transducer element in accordance with another embodiment of the present invention.
Figure 3A:
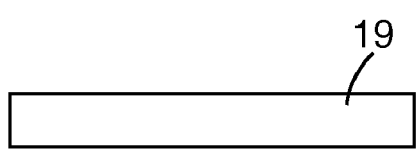
FIGS. 3A-3I show various configurations of a mass element that may be compliantly coupled to a transducer element in accordance with an embodiment of the present invention.
Figure 3F:
Figure 3B:
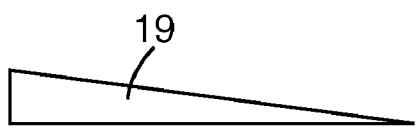
Figure 3G:
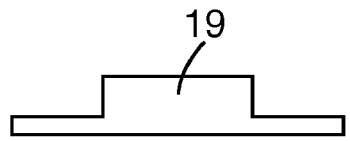
Figure 3C:
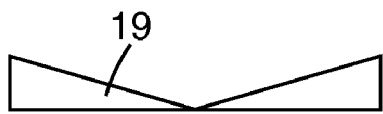
Figure 3H:
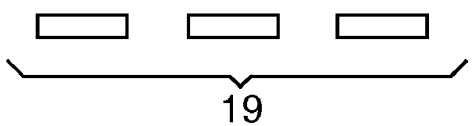
Figure 3D:
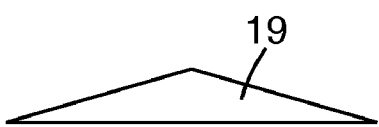
Figure 3I:
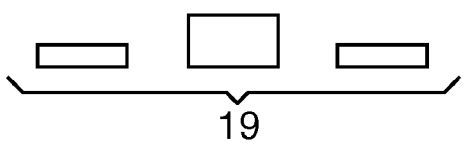
Figure 3E:
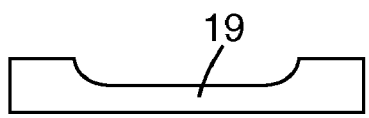

FIG. 2 is a diagram of a sensor 10 that incorporates a transducer assembly 11 in accordance with another embodiment of the present invention. Many of the features of sensor 10 shown in FIG. 2 are essentially those previously described with reference to FIG. 1. According to the embodiment shown in FIG. 2, the transducer assembly 11 includes a stiffening layer 17, which may be in the form of a sheet, film, membrane, or other type of stiff backing structure. The stiffening layer 17 is disposed between the mass 19 and intervening material 21. It is desirable that at least the surface of the stiffening layer 17 facing the transducer 14 possess a high reflection coefficient to acoustic waves of interest and their Fourier frequency range.

The stiffening layer 17 may include an adhesive or other form of fixation arrangement (e.g., mechanical coupling or weld) provided between the stiffening layer 17 and the mass 19. The intervening layer 21 preferably provides an adhesive interface for compliantly coupling the stiffening layer 17 to the transducer 14.

In one implementation, a polyvinyledene fluoride-like piezoelectric film 14 (e.g., a PVDF2 film) is encased in a polyester film as if in a pouch. The polyester film of about 1.5 thousandths of an inch thick may be disposed on each side of the PVDF2 film 14. In another implementation, the transducer element 14 may comprise a laminate structure. The laminate structure may comprise a piezoelectric film, a weight in film form, and one or more adhesive layers.

In general, the surface area of stiffening layer 17 is preferably coextensive with that of the transducing portion of the transducer 19. As is shown in FIG. 2, coverage of the mass 19 need not be coextensive with the transducing portion of the transducer 19, although such a configuration is contemplated. It is understood that the size, shape, and/or location of mass element 19 relative to the transducer 14 may change the frequency response and the sensitivity of transducer 14.

FIGS. 3A-3H show various configurations of mass 19. As is shown in FIGS. 3A-3H, the mass 19 may have a substantially uniform weight distribution profile relative to an x-y plane of the transducer 14. In some configurations, the mass 19 may have a substantially linear weight distribution profile relative to an x-y plane of the transducer 14. In other configurations, the mass 19 may have a non-linear weight distribution profile relative to an x-y plane of the transducer 14. The mass 19 may be a unitary mass or comprise two or more discrete mass arrangements. Many other configurations of mass 19 are contemplated, and FIGS. 3A-3H represent only some of these and are not to be regarded as limiting.

The transducer 14 is arranged in the transducer assembly 11 (e.g., as shown in FIGS. 1 and 2) so that a region defined between the respective ends of the transducer 14 is permitted to flex in response to forces acting on the transducer 14. Transducer 14 preferably incorporates material or elements that transduces mechanical deformation of the transducer 14 into a measurable electrical parameter. As was previously discussed, various transducers that modulate or generate a signal in response to deformation may be used, such as piezoelectric or piezoresistive material, strain gauges, capacitive or inductive elements, or a linear variable differential transformer, among others.

For example, depending upon the configuration of transducer 14, the type of transducing material or elements used, and the orientation and manner of deformation of the material/elements, a useful electrical response may be developed at electrodes or contacts located at various regions of the transducer element. Electrical connections can be made to conductive polymer, metallized foil, or conductive paint laminates or sandwiches containing the transducing material/element, for example. Useful measurable electrical parameters include a voltage, current, or a change in electrical resistance, for example.

It is known that certain semi-crystalline polymers, such as polarized fluoropolymer polyvinylidene fluoride (PVDF), have piezoresponsive properties, which may include piezoelectric response. PVDF is used in various sensors to produce a voltage as a function of force or displacement. Polymer resin piezoelectric materials are particularly useful because the polymers can be embodied as sensing elements which are both flexible and elastic, and develop a sense signal representing resiliently biased deformation when subjected to force.

In one embodiment, transducer 14 includes a thin strip of a suitable piezoelectric polymer as a sensing element. The sensing element of transducer 14 is oriented within the transducer assembly 11 so that the strip may be subject to deflection, which results in compression or tension of the sensing element in response to the applied force. Electrical contacts are made with the sensing element so that a voltage signal is produced in response to the force. Deformation of the sensing element of transducer 14 changes the relative positions of charges in the polymer chain or in the semi-crystalline lattice structure, thereby producing a voltage having an amplitude related (e.g., proportionally related) to the magnitude of the sensing element deformation.

The housing 12 shown in FIGS. 1 and 2 includes an interfacing portion 13. Bioacoustic signals, $S_{BS}$, produced from within the body, for example, are shown impinging on the interfacing portion 13. The interfacing portion 13 of the housing is configured to establish coupling with a body part during use of the sensor 10. For example, the interfacing portion 13 may be the surface of the housing 12 that comes into contact with a patient's chest or clothing covering the chest. The housing 12 also includes a non-interfacing portion 15, which may be a region of the housing 13 that faces the ambient environment during use of the sensor 10. The non-interfacing portion 15, which may be a separable cover, may incorporate acoustically absorptive material or other vibration attenuation material or arrangement.

The transducer assembly 11 is mounted within the housing 12 so that the transducer 14 is preferentially sensitive bioacoustic energy transmitted to the transducer 14 via the interfacing portion 13 relative to other portions of the housing 12, such as the non-interfacing portion 15. In the configuration shown in FIGS. 1 and 2, for example, transducer 14 has two opposing major surfaces. The transducer assembly 11 is mounted within the housing 12 so that the major surfaces of the transducer 14 are substantially parallel to the interfacing portion 13 of the housing 14. Other orientations are possible depending on the particular transducer and housing features and characteristics. Preferred orientations between the transducer 14 and interfacing portion 13 of the housing 12 are those that provide for increased signal-to-noise ratios.

The interfacing portion 13 of the housing 12 is preferably formed from, or incorporates, material that facilitates transmission of vibrations from the interfacing portion 13 to the transducer 14, such vibrations resulting from bioacoustic energy emanating from the body and impinging on the housing 12. The interfacing portion 13 preferably has sufficient integrity to support the transducer 14. It has been found that a wide variety of materials having varying pliability may be used, ranging from relatively pliable to substantially stiff.

Suitable or workable materials for the interfacing portion 13 include polymeric materials, metals including alloys, composites, crystalline or ceramic materials. For example, suitable or workable materials include viscoelastic materials, thermoplastic materials, thermosetting materials, paper materials (e.g., cardboard), and mineral materials (e.g., mica). Other examples include polycarbonate, styrene, ABS, polypropylene, aluminum, and other plastics and sheet metal alloys. It is understood that this listing of materials is for illustrative purposes only, and does not constitute an exhaustive identification of suitable or workable materials.

It is believed that use of relatively stiff material for the interfacing portion 13 increases the sensitivity of the transducer 14 to bioacoustic signals. It is also believed that a wide range of materials and stiffness provides for sufficient or enhanced transducer sensitivity.

A sensor 10 of the present invention may incorporate a noise cancellation arrangement by which ambient noise that could negatively impact sensing performance is effectively attenuated or eliminated. Sensor 10, such as that shown in FIGS. 1, 2, 4, and 5A-5C, may incorporate an optional auxiliary transducer 6 mounted within the housing 12. The auxiliary transducer 6 is preferably used to implement a noise cancellation methodology by the sensor 10. For example, the auxiliary transducer 6 may be mounted at a housing location that provides for preferential sensitivity to ambient noise. As shown in FIG. 2, for example, an auxiliary transducer 6 is mounted to the non-interfacing portion 15 (e.g., cover) of the housing 12. In this configuration, auxiliary transducer 6 is preferentially sensitive to vibrations resulting from ambient noise impinging on the non-interfacing portion 15 of the housing 12. The signal modulated or produced by the auxiliary transducer 6 may be used to cancel content of the signal modulated or produced by the transducer 14 that is attributable to ambient noise.

Various known methods of effecting noise cancellation using signals modulated or produced by auxiliary transducer 6 and transducer 14 may be used. The auxiliary transducer 6 may of the same or similar construction and configuration as transducer 14 or may be of a different construction and configuration.

Performance of sensor 10 may be enhanced by addition of an arrangement configured to modify a frequency response of the transducer 14. Such an arrangement may be a particular shape, stiffness, weight, or thickness of the transducer 14. Altering one or more of these parameters can modify the frequency response of the transducer 14. In a sensor implementation that includes multiple transducers, for example, each transducer may provide for a different frequency response by having at least one of the stiffness, weight, shape, and thickness differing from that of other transducers of the sensor. Providing masses 19 of different weight or weight distribution may also provide for transducers 14 having different frequency response.

Figure 4:
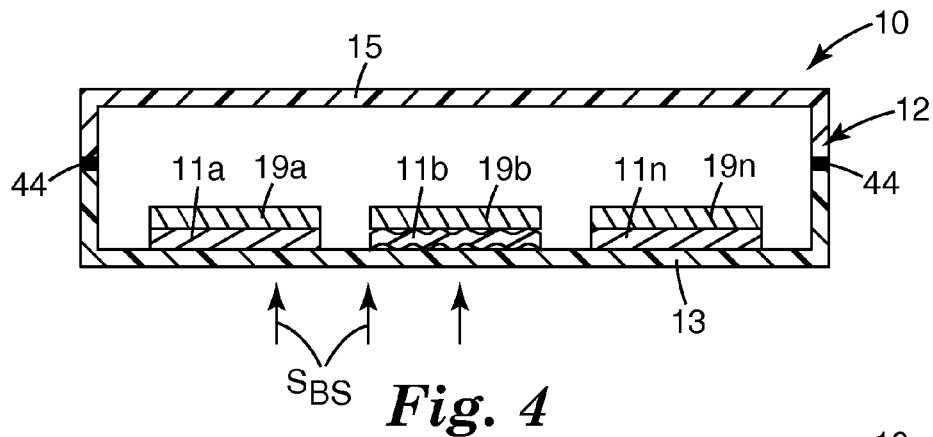
FIG. 4 is a diagram of a sensor that incorporates a multiplicity of transducer assemblies, the transducer of each transducer assembly configured to have a frequency response differing from other transducers of the sensor in accordance with an embodiment of the present invention.

FIGS. 4 and 5 are views of a sensor 10 that incorporate a multiplicity of transducer assemblies 11a-11n compliantly coupled to respective masses 19a-19n of different weight or weight distribution. The transducer of each transducer assembly 11a-11n is configured to have a frequency response differing from other transducers of the sensor 10. The transducer assemblies 11a-11n may be of the same or different design (planar, non-planar, or mix of both or other type).

For example, a first transducer of a sensor 10 may be properly weighted to be preferentially sensitive to heart sounds, while a second transducer of the sensor 10 may be properly weighted to be preferentially sensitive to lung sounds. By way of further example, a first transducer of a sensor 10 may be properly weighted to be preferentially sensitive to sounds associated with normal heart valve closure activity in the frequency range 10 to 200 Hz, while a second transducer of the sensor 10 may be properly weighted to be preferentially sensitive to sounds associated with abnormal heart valve closure activity (e.g., valve stenosis) in the 10 to 700 Hz range.

As was discussed previously, the frequency response of a transducer is governed by several parameters, most notably the shape, stiffness, weight, and thickness of the effective transducing element of the transducer. Altering one or more of these parameters can modify the frequency response of the transducer. In the embodiment shown in FIG. 4, at least one of these parameters is different for each transducer assembly 11a-11n, resulting in each transducer of the transducer assemblies 11a-11n having a different frequency response. It is appreciated that other parameters can be varied among the transducer assemblies 11a-11n to achieve differing frequency responses.

It is appreciated that other parameters of the sensor or sensor housing can be varied relative to the transducer assemblies 11a-11n in order to achieve differing frequency responses and/or sensitivities. The housing 12, and more specifically the interfacing portion 13, may include features that provide for a differing frequency response across an array of transducer assemblies 11a-11n. For example, the thickness, material, or other aspect of a region of the interfacing portion 13 that supports or otherwise influences each transducer assembly 11a-11n may be varied. Elements of varying shape and material may be inserted into the interfacing portion 13 so as to influence the frequency response and/or sensitivity of each transducer assembly 11a-11n in a desired manner As such, differences in the frequency response and/or sensitivity of multiple transducers assemblies 11a-11n may be achieved at least in part by providing for differences in the housing construction or material in regions that support or influence of the transducers assemblies 11a-11n.

Figure 5A:
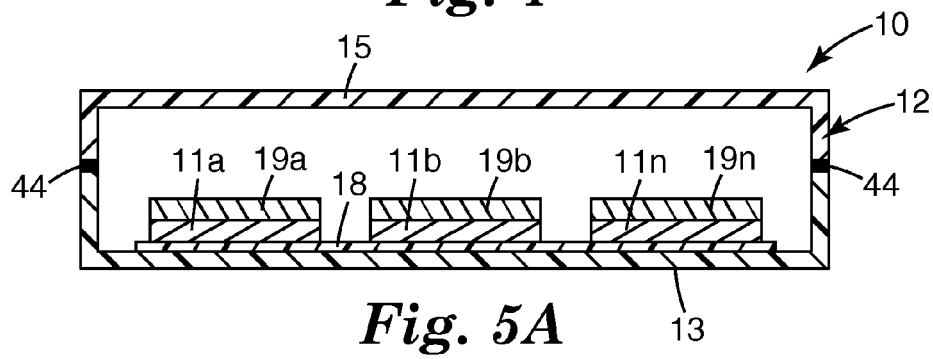
FIG. 5A is a diagram of a sensor that incorporates a multiplicity of transducers mounted to a common anchoring arrangement, the transducers configured to have a frequency response differing from other transducers of the sensor in accordance with an embodiment of the present invention.

FIG. 5A is a diagram of a sensor 10 that incorporates a multiplicity of transducer assemblies 11a-11n compliantly coupled to respective masses 19a-19n mounted to a common anchoring arrangement 18. In this illustrative embodiment, the anchoring arrangement 18 may be a stiff material to which each of the transducer assemblies 11a-11n are mounted. This configuration may simplify manufacturing of the transducer section of the sensor 10 and installation of the transducer section into the housing 12 during assembly.

Figure 5B:
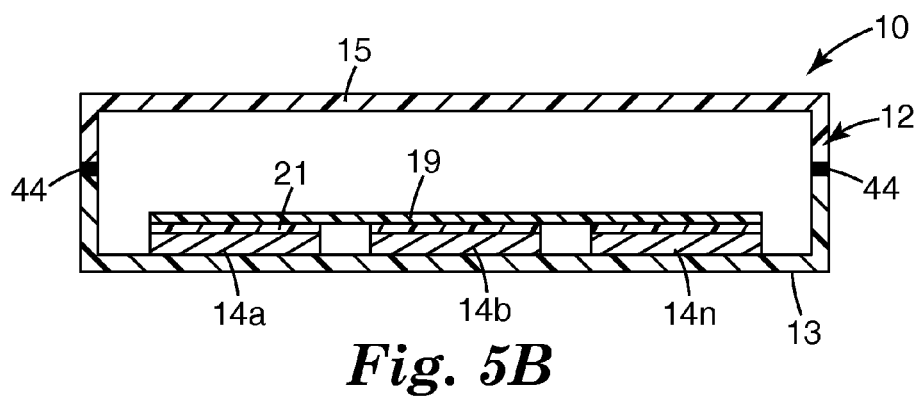
FIG. 5B is a diagram of a sensor that incorporates a multiplicity of transducer assemblies and a unitary mass element compliantly coupled to the transducer element of each transducer assembly, the transducers configured to have a frequency response differing from other transducers of the sensor in accordance with an embodiment of the present invention.
Figure 5C:
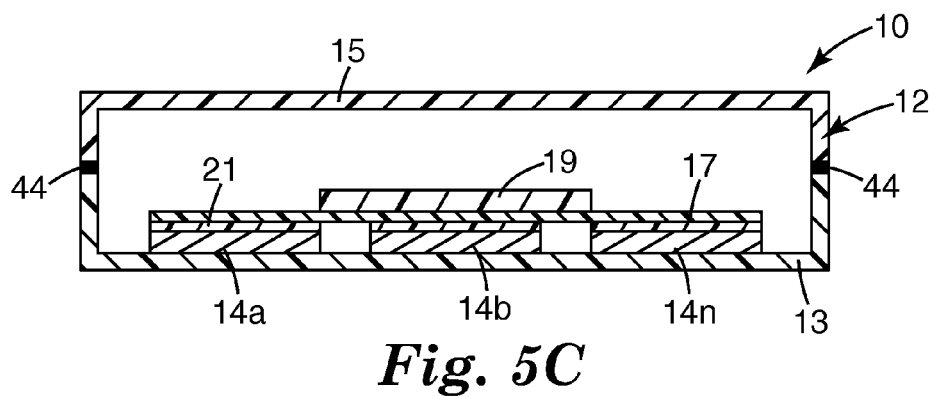
FIG. 5C is a diagram of a sensor that incorporates a multiplicity of transducer assemblies, a stiffening sheet or membrane, and a unitary mass element compliantly coupled to the transducer element of each transducer assembly, the transducers configured to have a frequency response differing from other transducers of the sensor in accordance with an embodiment of the present invention.

FIGS. 5B and 5C show two illustrative configurations of a multiple transducer sensor 10 in accordance with embodiments of the present invention. FIG. 5B is a diagram of a sensor 10 that incorporates a multiplicity of transducer assemblies 11a-11n and a unitary mass 19 compliantly coupled to the transducer 14a-14n of each transducer assembly 11a-11n via intervening material 21. The transducers 14a-14n are preferably configured to have a frequency response differing from other transducers 14a-14n of the sensor 10.

FIG. 5C is a diagram of a sensor 10 that incorporates a multiplicity of transducer assemblies 11a-11n, a stiffening layer 21, and a unitary mass 19 compliantly coupled to the transducer 14a-14n of each transducer assembly 11a-11n via intervening layer 21. The transducers 14a-14n are preferably configured to have a frequency response differing from other transducers 14a-14n of the sensor 10.

It is understood that individual transducers of a given multi-transducer assembly are preferably coupled to the sense/detection circuitry or processor of the sensor via individual channels, with appropriate buffering provided for each channel. It is understood that one needs to be careful in preventing or filtering later any cross talk that may occur amongst the various transducers 14a-14n. Although such channels are typically defined by one or more conductors dedicated for each transducer, various time or frequency multiplexing techniques may be used to reduce to the complexity of the sensor's wiring scheme.

Clinicians readily appreciate that detecting relevant cardiac symptoms and forming a diagnosis based on sounds heard through a stethoscope, for example, is a skill that can take years to acquire and refine. The task of acoustically detecting abnormal cardiac activity is complicated by the fact that heart sounds are often separated from one another by very short periods of time, and that signals characterizing cardiac disorders are often less audible than normal heart sounds.

It has been reported that the ability of medical students to recognize heart murmurs correctly is poor. In one study, it was found that only 13.5±9.8% students were able to diagnose heart murmurs correctly, and that this does not improve with subsequent years of training by lectures, demonstration of heart sounds, and then clinical exposures. It has also been found, through psychoacoustic experimentation, that a sound needs to be repeated from 1200-4400 times for the brain to recognize differences. Using this information, studies have been performed to evaluate the effect of heart sound repetition on a doctor's ability to diagnose correctly. One such study was performed with 51 medical student doctors diagnosing four basic cardiac murmurs, where each murmur was repeated 500 times. Significant improvement (85±17.6%) of auscultatory proficiency was observed, demonstrating that repeating the heart sounds of interest some 500 times resulted in increased proficiency to correctly recognize basic cardiac murmurs.

It should be appreciated that there are more than 40 different known heart "murmur" sounds. This would make it challenging for doctors to listen to each heart sound 500 times and remember each of the 40 known heart sounds, as the brain has a tendency to loose the memory if the sound has not been heard for a long time.

The decline in the diagnostic skill of cardiac auscultation has contributed to a situation for both patients and physicians to rely on alternative diagnostic methods. It has been reported that nearly 80% of patients referred to cardiologists have normal hearts or only benign heart murmurs. Such false positives constitute a significant waste of time and expense for both patients and cardiologists.

A bioacoustic sensor of the present invention may be implemented to be sensitive to heart sounds of varying types and characteristics. For example, a sensor may incorporate several transducers, each of which is preferentially sensitive to a frequency or range of frequencies associated with one or a number of known heart sounds. For example, individual transducers may be "tuned" to detect particular heart murmurs. A switching or scanning technique may be employed by which each transducer of an array of transducers is selectively enabled for listening by the clinician or for output to a display/auditory device, such as by use of a wireless communication link.

In a more complex implementation, sound profiles of the 40 or more known heart sounds may be developed (e.g., signal morphological profiles or frequency spectrum profiles) . A processor, such as a digital signal processor, may perform a comparison between detected heart sounds and heart sound profiles of a library of such profiles to determine presence or absence of particular heart sounds emanating from the patient. Various algorithms, such as correlation or pattern recognition algorithms, may be employed to perform the comparison.

The capability of adjusting the frequency response of the bioacoustic sensor 10 of the present invention advantageously allows a single sensor to have broadband sensitivity to a wide spectrum of body sounds, and the ability to target body sound frequencies of particular interest.

Figure 6:
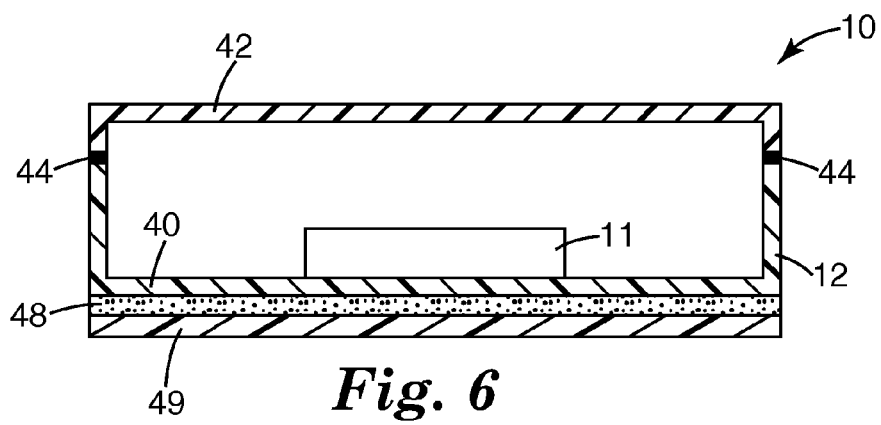
FIG. 6 is a diagram of a sensor that incorporates a transducer mounted in a housing, the housing including an adhesive layer that provides for intimate coupling between the housing and a body part during use in accordance with an embodiment of the present invention.

FIG. 6 is a diagram of a sensor 10 that incorporates a transducer assembly 11 of the present invention disposed in a housing 12. The housing 12 includes an adhesive layer 48 that provides for intimate and secured coupling between the sensor housing 12 and a body part during use. A peel-away liner 49 may cover the adhesive layer 48 and be removed prior to use of the sensor 10. The adhesive layer 48 preferably provides for good acoustic coupling between the sensor 10 and the patient's body part (e.g., skin or outer clothing) For example, adhesives similar to the pressure sensitive adhesive tapes used in the construction of electrocardiogram (ECG) electrodes to be adhered to skin may be used. One such tape is Micropore tape with adhesive, No. 9914, non-woven skin tape, available from 3M, St. Paul, Minn. A sensor configured according to FIG. 6 may be particularly useful in the context of a disposable sensing device, such as a disposable stethoscope.

The housing 12 shown in FIG. 6 is a two-part housing that includes a base 40 and a cover 42. The base 42 is preferably formed of a relatively stiff material, as the base 42 incorporates an interfacing portion as described hereinabove. The cover 42 may be formed from the same or different material as the base 40, and attached to the base 40 using a known coupling arrangement. A compliant interface 44 may be formed between the base 40 and cover 42. The compliant interface 44 is formed of a material that attenuates vibrations transmitted along or through the cover 42, typically produced from sources in the ambient environment. Also, and as previously discussed, cover 42 may be formed from acoustically absorptive material that aids in reducing transducer excitation due to ambient noise. Provision of vibration isolation/attenuation between the cover 42 and base 40 advantageously attenuates vibrations produced from such ambient sources (e.g., non-body produced sounds), thus increasing the sensitivity of the senor 10 to body produced sounds.

Figure 7:
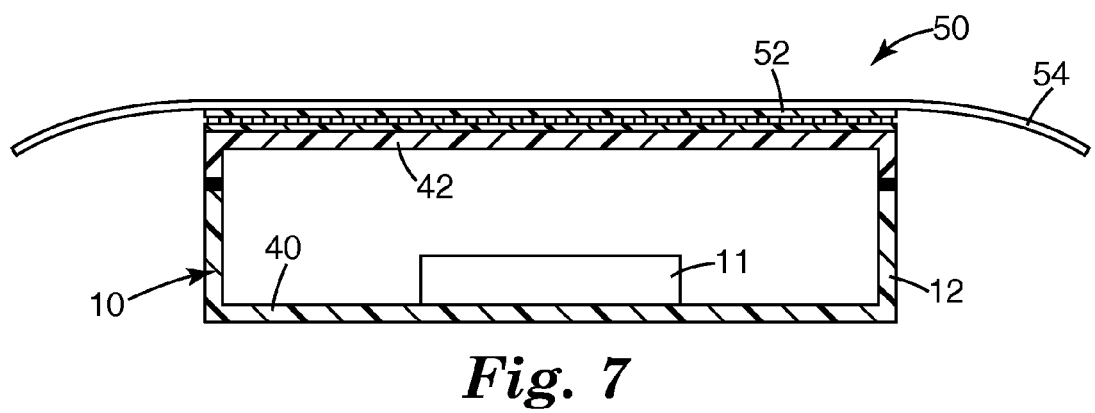
FIG. 7 is a diagram of a sensor that incorporates a transducer mounted in a housing, the housing including an elastic fixation arrangement that provides for intimate coupling between the housing and a body part during use in accordance with an embodiment of the present invention.

FIG. 7 is a diagram of a sensor 10 that incorporates a housing 12 having a fixation arrangement 50. The fixation arrangement 50 facilitates fixation of the sensor 10 to a patient's body part during use and easy removal from the patient after use. In the embodiment shown in FIG. 7, the fixation arrangement 50 includes one or more elastic bands 54 that are coupled to the housing 12 of the sensor 10. The elastic bands 54 are of sufficient length and elasticity to extend around the patient's body part of interest. The ends of the elastic bands 54 are provided with a suitable coupling arrangement that allows for secured engagement of sensor 10 to the patient during use. In an alternative configuration, the fixation arrangement 50 may include one or more strips of adhesive tape, which may be represented by adhesive (elastic or non-elastic) bands or strips 54 in FIG. 7.

The signal processing circuitry 94 may perform more sophisticated analysis of bioacoustic signals received from the sensor 10, such as body sound profile matching as discussed above. The signal processing circuitry 94 may perform various forms of statistical analysis on signals produced by the sensor. In such configurations, the signal processing circuitry 94 may include a digital signal processor. Alternatively, or in addition, an external system 114 may perform all or some of such signal processing and analyses. The external system 114 may include a display, sound system, printer, network interface, and communications interface configured to establish uni- or bi-directional communication with the communications device 112 disposed in the main housing 115 of the stethoscope 90.

Figure 8:
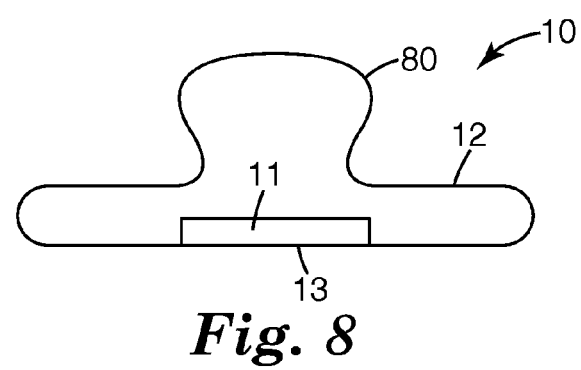
FIG. 8 is a diagram of a sensor that incorporates a transducer mounted in a housing, the housing shape configured for ease of hand manipulation to facilitate intimate coupling between the housing and a body part during use in accordance with an embodiment of the present invention.

FIG. 8 is a diagram of a sensor 10 that incorporates a housing 12 having a shape configured for ease of hand manipulation to facilitate manual coupling between the housing 12 and a body part during use in accordance with an embodiment of the present invention. The shape of the housing 12 may be ergonomically tailored to the specific use of the sensor. The housing 12 shown in FIG. 8 may facilitate ease of hand-held manipulation of the sensor 10. For example, a clinician may grasp the handle projection 80 of the housing 12 and apply the interfacing portion 13 of the housing to the patient's skin or outer clothing The sensor 10 may be held in place by the clinician during the evaluation. It is understood that other housing shapes are contemplated.

Figure 9A:
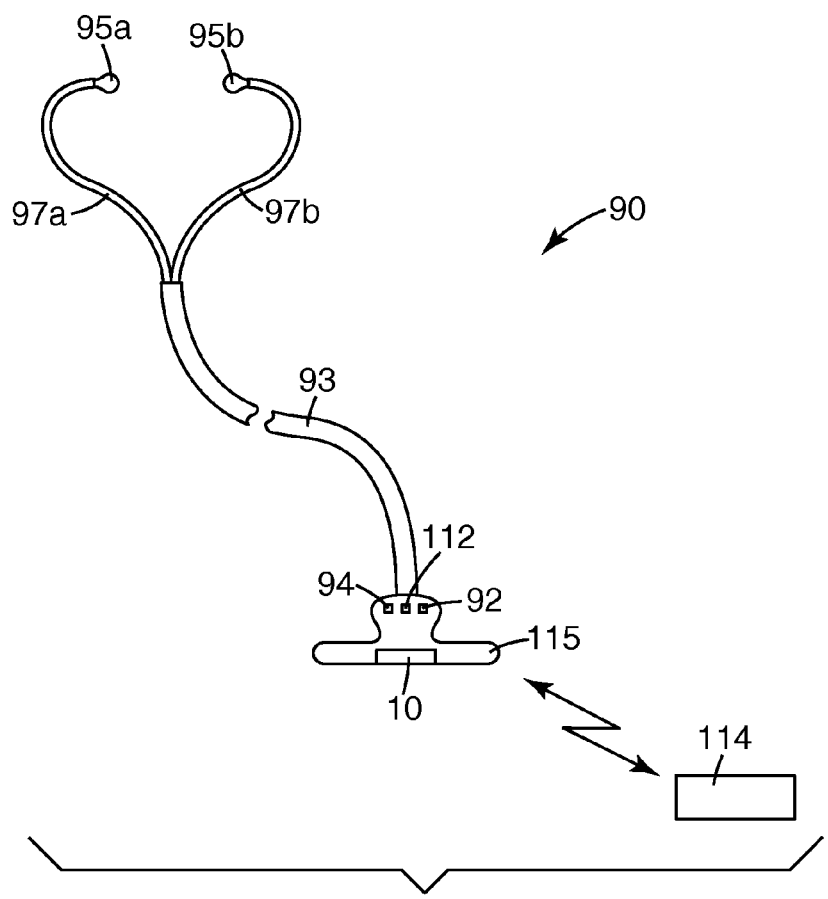
FIG. 9A shows a stethoscope that incorporates a sensor of the present invention.

FIG. 9a shows a stethoscope that incorporates a sensor of the present invention. The stethoscope 90 is an electronic stethoscope configured to include traditional components, such as a pair of ear pieces 95a, 95b, ear tubes 97a, 97b, and a main tube 93. The main tube 93 is coupled to a main housing 115, within which a sensor 10 of a type previously described is disposed. Other components that may be disposed in the main housing 115 include a power source 92, signal processing circuitry 94, and a communications device 112. The signal processing circuitry 94 may perform more sophisticated analysis of bioacoustic signals received from the sensor 10, such as body sound profile matching as discussed above. Alternatively, or in addition, an external system 114 may perform such signal processing and analyses. The external system 114 may include a display, sound system, printer, network interface, and communications interface configured to establish uni- or bi-directional communication with the communications device 112 disposed in the main housing 115 of the stethoscope 90.

Communications device 112 may be implemented to establish a conventional radio frequency (RF) link that is traditionally used to effect communications between local and remote systems as is known in the art. The communication link between communications device 112 and external system 114 may be implemented using a short-range wireless communication interface, such as an interface conforming to a known communications standard, such as a Bluetooth standard, IEEE 802 standards (e.g., IEEE 802.11), or other public or proprietary wireless protocol.

Figure 9B:
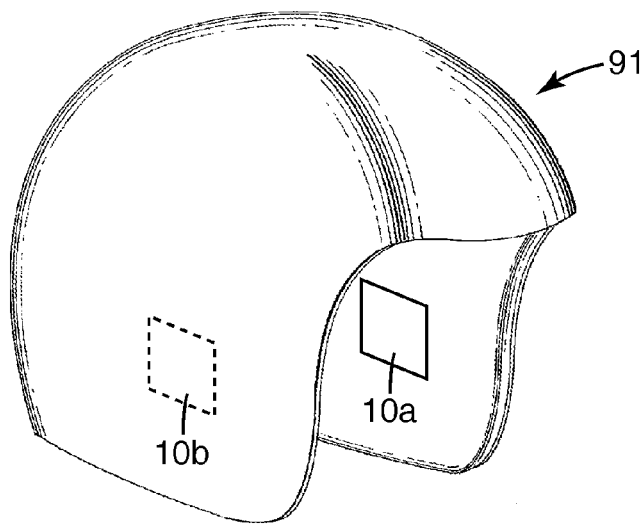
FIG. 9B shows a helmet that incorporates a pair of sensors of the present invention.

FIG. 9b shows a helmet 91 that incorporates sensors 10a and 10b of a type described herein. According to the embodiment shown in FIG. 9b, sensors 10a and 10b may be implemented to provide enhanced hearing by the wearer of the helmet 91, and may further provide for ambient noise cancellation such as in the manner described previously with reference to FIG. 2. Sensors 10a and 10b or other sensor may be implemented to serve as a voice pick-up, the performance of which may be enhanced by an ambient noise cancellation capability of a type previously described. Various devices and apparatuses that may be implemented to include one or more sensors of the present invention are disclosed in U.S. Pat. Nos. 4,756,028; 5,515,865; 5,853,005; and D433,776, which are hereby incorporated herein by reference.

Figure 10:
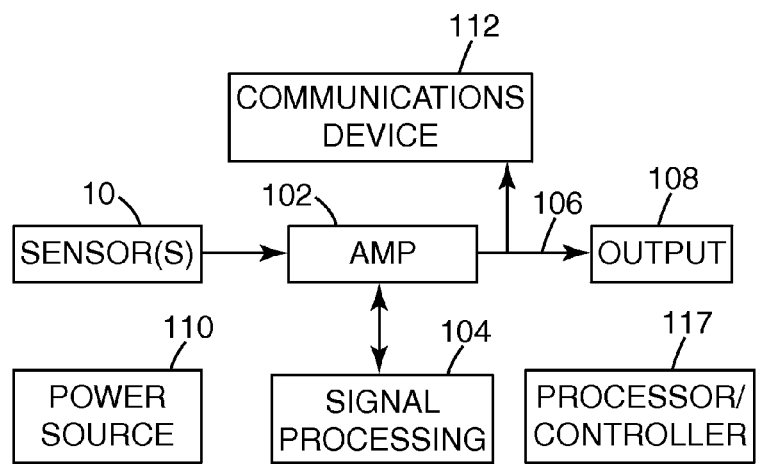
FIG. 10 is a block diagram of circuitry of a sensor in accordance with an embodiment of the present invention.

FIG. 10 is a block diagram showing various components of a sensor 10 in accordance with an embodiment of the present invention. According to the embodiment shown in FIG. 10, one or more sensors 10 of a type described previously is/are coupled to an amplifier 102, typically in accordance with a differential configuration. In an implementation that employs several sensors 10 or multiple transducers, each may be coupled to a separate amplifier 102. The amplifier 102 may include a first stage that is located on the transducer assembly, such as on or near the anchoring end of the transducer. This first amplifier stage, if needed, may serve primarily to convert a high impedance of the transducer, such as a piezoelectric transducer, to a low, less noise susceptible impedance. A second stage amplifier may be used to amplify the sense signal produced at the output of the first stage.

Signal processing circuitry 104 may be coupled to the amplifier 102. The sophistication of the signal processing circuitry 104 may vary from simple to complex. For example, signal processing circuitry 104 may include a simple notch filter having a center frequency of 60 Hz for purposes of attenuating noise due to common power sources. Signal processing circuitry 104 may include one or more bandpass filters that enhance the sensitivity and/or signal-to-noise ratio of transducer signal content of interest.

More sophisticated filtering may be performed on the sense signal to enhance detection of particular body sounds of interest. Such filters may include analog and/or digital filters. Relatively sophisticated analog and digital signal processors may be used to provide for more complex signal processing, such as pattern recognition, source separation, feature correlation, and noise cancellation.

A communications device 112 may be coupled to an output of the amplifier 102. The communications device 112 may be of a type previously described that provides for a communication link between communications device 112 and external system. A power source 110 provides power to the active components of the sensor. A processor/controller 117 may be incorporated to coordinate the various functions of the componentry shown in FIG. 10. Sense signals produced at the output 108 of amplifier 102 are communicated to downstream components via conductor(s) 106, which may be electrical or optical conductors.

The processor/controller 117 may be configured to perform various diagnostic and calibration operations. For example, it may be desirable to equalize the gain response of each transducer of a given sensor. It may also be desirable to perform a frequency response calibration to "tune" or adjust the "tuning" of the frequency response of the transducer(s). The gain and/or frequency response of each transducer may be adjusted during a calibration routine so that each is at a pre-established amplitude and/or exhibits a desired frequency response. Calibration may be initiated before or during use of the sensor, and may be coordinated by the processor/controller 117. In one configuration, an excitation source may be included with the sensor (internal or external) that generates excitation signals having known characteristics, allowing for relatively easy and accurate calibration of transducer gain and/or frequency response.

Figure 11:
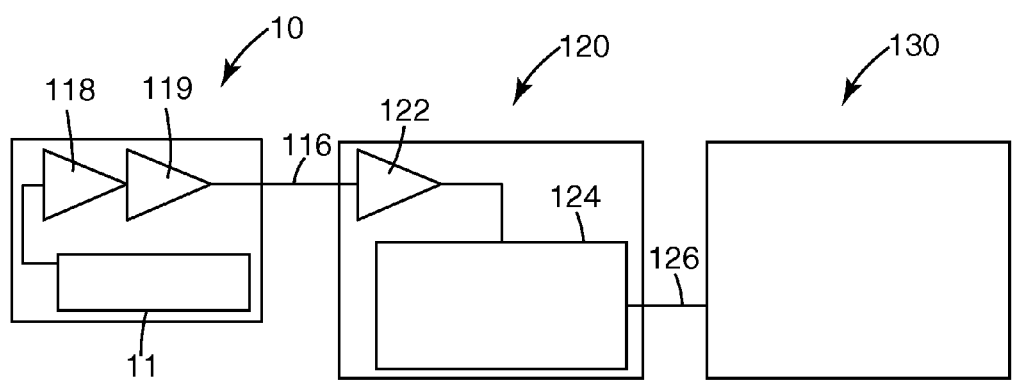
FIG. 11 is a diagram of circuitry for communicating signals produced by a sensor using optical fiber in accordance with an embodiment of the present invention.

According to one embodiment, and as shown in FIG. 11, an impedance conversion amplifier 118 may be implemented at or near to the transducer 11 that is directly interfaced to an analog fiber optic transmitter 119. The output of the fiber optic transmitter 119 is connected to an optical guide 116, which is connected to receiver circuitry 120. Receiver circuitry 120 includes an analog fiber optic receiver 122 that converts the light signal transmitted via the optical guide 116 back to an electrical signal. The output of the optical receiver 122 is coupled to circuitry 124 that may include additional amplification, signal processing and/or a system to record the signal/data communicated over the optical guide 116. Receiver circuitry 120 may be coupled to an additional device or circuitry 130 via electrical or wireless link 126. The additional device or circuitry 130 may be an audio output device, such as earphones, an electronic information device, such as a PDA or PC, a display device, or a network interface.

The housing in FIG. 11 that contains the piezoelectric transducer 14 may contain a small battery to power the impedance conversion amplifier 112 and optical transmitter 114, or two small wires can be included in a bundle with the fiber optic guide or cable 116 for supplying power to these and other active components.

Signal conditioning or processing circuitry can be located at, near or be integrally associated with the transducer 11. For example, the transducer 11 and the signal processing circuitry may be a unitary structure. The signal conditioning or processing circuitry may include one or more of amplification circuitry, such as buffer, gain and/or impedance matching amplification circuitry, filter circuitry, signal conversion circuitry, and more sophisticated circuitry.

A bioacoustic sensor of the present invention provides for exceptional sensitivity and signal-to-noise ratio by use of a transducer of the type described herein and a mass that offers stiffening to the transducer. The performance of the sensor was verified using a phonocardiogram. Different heart sounds related to different diseases were regenerated in terms of sound, via a compact disk, and phonocardiogram (PCS) using this sensor. There was little difference between the original sound recorded on the CD and the regenerated sensor sounds. The sensor was found to be so sensitive that it can achieve a very good signal-to-noise ratio even when placed over the clothing of the patient.

The foregoing description of the various embodiments of the invention has been presented for the purposes of illustration and description. It is not intended to be exhaustive or to limit the invention to the precise form disclosed. Many modifications and variations are possible in light of the above teaching. For example, sleep disorders by themselves and as indicators of more serious neurological diseases are on the rise. Sleep apnea at all ages and sudden infant death syndrome in babies are also on the rise while their etiology is being identified. A method of diagnosis may involve monitoring body movements and breath/lung sounds of patients with the above indications, which may be readily performed using sensors of the kind described herein. Also, a sensor of the present invention may be used in applications other than bioacoustic sensing applications. It is intended that the scope of the invention be limited not by this detailed description, but rather by the claims appended hereto.

What is claimed is:

1. A bioacoustic sensor, comprising:
   a housing comprising an interfacing portion configured to establish coupling with a body part during use;
   a transducer assembly comprising;
   a transducer element coupled to the interfacing portion of the housing and configured to sense sounds produced by matter of biological origin, the transducer element configured to modulate or generate a signal in response to deformation of the transducer element;
   one or more conductors coupled to the transducer element;
   a mass element compliantly coupled to a surface of the transducer element; and
   intervening material disposed between the transducer element surface and the mass element, the intervening material allowing for differential motion between the transducer element surface and the mass element during excitation of the transducer element, wherein the mass element comprises a mass and a stiff sheet, film or membrane having a first surface and a second surface, the first surface arranged to contact the intervening material and the mass disposed adjacent the second surface, and
   wherein the transducer assembly is mounted on an inner surface of the interfacing portion within the housing so that the transducer element is preferentially sensitive to bioacoustic energy transmitted to the transducer element via the interfacing portion.

2. The sensor of claim 1, wherein the mass element, intervening material, and transducer element are configured to amplify a signal producible by the transducer element.

3. The sensor of claim 1, wherein the mass element, intervening material, and transducer element are configured to allow for mechanical deformation of the transducer element in response to bioacoustic energy impinging on the transducer element.

4. The sensor of claim 1, wherein at least a surface of the mass element facing the transducer element has a high reflection coefficient to acoustic waves.

5. The sensor of claim 1, wherein the intervening material is capable of transmitting sound signals.

6. The sensor of claim 1, wherein the intervening material comprises an adhesive.

7. The sensor of claim 1, wherein the intervening material has a low acoustic impedance.

8. The sensor of claim 1, wherein the mass element covers substantially all of an effective transducing portion of the transducer element surface.

9. The sensor of claim 1, wherein the intervening material comprises a foam material.

10. The sensor of claim 1, wherein at least the first surface of the stiff sheet, film or membrane has a high reflection coefficient to acoustic waves.

11. The sensor of claim 1, wherein the mass element comprises metal or non-metallic material.

12. The sensor of claim 1, wherein the mass element has a substantially uniform weight distribution profile relative to an x-y plane of the transducer element.

13. The sensor of claim 1, wherein the mass element has a substantially non-uniform weight distribution profile relative to an x-y plane of the transducer element.

14. The sensor of claim 1, wherein the mass element comprises a plurality of discrete mass arrangements.

15. The sensor of claim 1, wherein the mass element is a unitary mass element.

16. The sensor of claim 1, wherein the transducer element comprises a polymeric piezoelectric film.

17. The sensor of claim 1, wherein the transducer element comprises piezoresistive material, one or more strain gauges, one or more capacitive elements, ceramic material or crystalline material.

18. The sensor of claim 1, wherein the transducer element further comprises a laminate structure, the laminate structure comprising piezoelectric film, a weight in film form, and one or more adhesive layers.

19. The sensor of claim 1, wherein components of the transducer element are embedded in a mass of the intervening material.

20. The sensor of claim 1, wherein the sensor is configured to have broadband sensitivity to normal and abnormal biological sounds.

21. A sensor unit comprising a plurality of the transducer elements according to claim 1, wherein each of the plurality of transducer elements is configured to have a frequency response differing from that of at least one other transducer element of the plurality of transducer elements.

22. A sensor unit of claim 21, wherein each of the plurality of transducer elements has a stiffness, weight, shape, and thickness, at least one of the stiffness, weight, shape, and thickness of each of the plurality of transducer elements differing from that of at least one other transducer element of the plurality of transducer elements.

23. A bioacoustic sensor, comprising:
a housing including an interfacing portion configured to establish coupling with a body part during use;
a transducer assembly comprising;
a transducer element coupled to the interfacing portion of the housing and configured to sense sounds produced by matter of biological origin, the transducer element configured to modulate or generate a signal in response to deformation of the transducer element;
one or more conductors coupled to the transducer element;
a mass element compliantly coupled to a surface of the transducer element; and
intervening material disposed between the transducer element surface and the mass element, the intervening material allowing for differential motion between the transducer element surface and the mass element during excitation of the transducer element, wherein the intervening material includes a foam material, and
wherein the transducer assembly is mounted on an inner surface of the interfacing portion within the housing so that the transducer element is preferentially sensitive to bioacoustic energy transmitted to the transducer element via the interfacing portion.

24. The transducer of claim 23, wherein the foam material comprises a low-density polyurethane foam.

25. The transducer of claim 23, wherein the intervening material includes an adhesive.

26. A bioacoustic sensor, comprising:
a housing comprising an interfacing portion configured to establish coupling with a body part during use;
a transducer assembly comprising;
a transducer element coupled to the interfacing portion of the housing and configured to sense sounds produced by matter of biological origin, the transducer element configured to modulate or generate a signal in response to deformation of the transducer element;
one or more conductors coupled to the transducer element;
a mass element compliantly coupled to a surface of the transducer element; and
intervening material disposed between the transducer element surface and the mass element, the intervening material allowing for differential motion between the transducer element surface and the mass element during excitation of the transducer element,
wherein the transducer assembly is mounted on an inner surface of the interfacing portion within the housing so that the transducer element is preferentially sensitive to bioacoustic energy transmitted to the transducer element via the interfacing portion,
and wherein the sensor is configured to have broadband sensitivity to normal and abnormal biological sounds.

\* \* \* \* \*

UNITED STATES PATENT AND TRADEMARK OFFICE
CERTIFICATE OF CORRECTION

PATENT NO. : 8,333,718 B2
APPLICATION NO. : 13/211178
DATED : December 18, 2012
INVENTOR(S) : Hatim Mohamed Carim It is certified that error appears in the above-identified patent and that said Letters Patent is hereby corrected as shown below:

In the Specifications:
Column 2, Line 32, Delete "polyvinyledene" and insert -- polyvinylidene --, therefor.

Column 7
Line 50, Delete "polyvinyledene" and insert -- polyvinylidene --, therefor.
Line 66, Delete "FIGS. 3A-3H" and insert -- FIGS. 3A-3I --, therefor.
Line 67, Delete "FIGS. 3A-3H," and insert -- FIGS. 3A-3I, --, therefor.

Column 8, Line 9, Delete "FIGS. 3A-3H" and insert -- FIGS. 3A-3I --, therefor.

Column 10, Line 58, Delete "manner As" and insert -- manner. As --, therefor.

Column 11, Line 64, Delete "loose" and insert -- lose --, therefor.

Column 12
Line 41, Delete "clothing) For" and insert -- clothing). For --, therefor.
Line 67, Delete "senor" and insert -- sensor --, therefor.

Column 13, Line 40, Delete "clothing The" and insert -- clothing. The --, therefor.

Signed and Sealed this
Fourth Day of June, 2013

Teresa Stanek Rea
*Acting Director of the United States Patent and Trademark Office*